United States Patent [19]

Naito et al.

[11] Patent Number: 5,759,763
[45] Date of Patent: Jun. 2, 1998

[54] METHOD FOR CRYOPRESERVATION OF PRIMORDIAL GERM CELLS AND GERM CELLS

[75] Inventors: Mitsuru Naito; Atsushi Tajima, both of Tsukuba; Yoshiaki Yasuda; Takashi Kuwana, both of Kumamoto, all of Japan

[73] Assignee: Director of National Institute of Animal Industry, Ministry of Agriculture, Forestry and Fisheries, Ibaraki-ken, Japan

[21] Appl. No.: 609,168

[22] Filed: Mar. 4, 1996

Related U.S. Application Data

[63] Continuation of Ser. No. 381,569, Jan. 31, 1995, abandoned.

[30] Foreign Application Priority Data

Jan. 31, 1995 [JP] Japan .................................. 6-288638

[51] Int. Cl.$^6$ .......................... A01N 1/02; C12N 5/00
[52] U.S. Cl. .......................... 435/1.1; 435/2; 435/240.2; 424/561; 600/34
[58] Field of Search .................... 435/1, 2, 240.2; 424/93.2, 93.21, 93.7, 561, 582; 600/34

[56] References Cited

U.S. PATENT DOCUMENTS 5,342,776   8/1994   Bolnet ........................... 435/240.2

FOREIGN PATENT DOCUMENTS

WO 90/11355   10/1990   WIPO.

OTHER PUBLICATIONS

Molecular Reproduction and Development, vol. 39, No. 2, pp. 153–161, Oct. 1, 1994, Mitsuru Naito, et al., "Production of Germline Chimeric Chickens, with High Transmission Rate of Donor–Derived Gametes, Produced by Transfer of Primodial Germ Cells".

British Poultry Science, vol. 33, pp. 449–453, 1992, M. Naito, et al., "Preservation of Quail Blastoderm Cells in Liquid Nitrogen".

Theriogenology, vol. 33, No. 1, p. 272, Jan. 1990, F. Leichthammer, et al., "In Vitro Culture and Cryopreservation of Farm Animals' Primodial Germ Cells".

Theriogenology, vol. 40, pp. 509–519, 1993, A. Tajima, et al., "Production of Germ Line Chimera by Transfer of Primordial Germ Cells in the Domestic Chicken (Gallus Domesticus)".

H. Eyal–Giladi et al. Developmental Biology, vol. 49, p. 321–337 (1976).

V. Hamburger et al. Developmental Dynamics, vo. 195, pp.231–272 (1992).

Tajima A., Production of Germ Line Chimera by Transfer of Primordial Germ Cells in the Domestic Chicken. Theriogenology 40: 509–519.

Leibo S., Techniques for Preservation of mammalian Germ Plasm, Animal Biotech 3(1) 139–153 (1992).

Naito M., Production of Germline Chimeric Chickens, With High Transmission Rate of Donor–Derived Gametes, Produced by Transfer of Primoridal Germ Cells, Molecular Reproduction and Development 39:153–161.

Petitte J., Accessing the Genome of the Chicken . . . Manipulation of the Avian Genome CRC Press pp. 81–101 1993.

Naito M., Preservation of Chick Primordial Germ . . . J of Repro & Fertil (1994) 102 321–325.

Subramoniam T., Cryopreservation of Crustacean . . . Proc Indian Natn Sci Acad B60(3) pp. 229–236 1994.

*Primary Examiner*—Ralph Gitomer
*Attorney, Agent, or Firm*—Oblon, Spivak, McClelland, Maier & Neustadt, P.C.

[57] ABSTRACT

Cryopreservation of primordial germ cells and germ cells, in which primordial germ cells or germ cells are separated from bird embryos before meiosis and are then suspended and frozen in a freezing medium containing a cryoprotective agent is useful for the conservation of species of birds, for the protection of rare species which are in danger of extinction and also for the production of transgenic animals, the production of novel animals having gene markers on a cellular level, the production of animals useful as disease models, the production of useful substances by genetic engineering, and the development of test methods for toxicity to germ-line cells.

7 Claims, No Drawings

METHOD FOR CRYOPRESERVATION OF PRIMORDIAL GERM CELLS AND GERM CELLS

This application is a continuation of application Ser. No. 08/381,569, filed on Jan. 31, 1995, now abandoned.

FIELD OF THE INVENTION

The present invention relates to a method for cryopreservation of primordial germ cells and germ cells and, more precisely, to a method for cryopreservation of primordial germ cells and germ cells which are used as materials for developmental biotechnology and are used for conservation of species, etc. in the fields of agriculture, medicine, etc.

BACKGROUND OF THE INVENTION

In the field of developmental biotechnology, germ-line cells are generally utilized when various manipulations are applied to cells so as to transmit their effects down to their offspring or when the conservation of species is desired to be conducted efficiently.

Of such germ-line cells, primordial germ cells or germ cells before meiosis, as having all genes of the species, are most advantageously utilized.

Recently, a method for separating primordial germ cells and a method of transplanting them have been developed especially in birds. If various genetic manipulations are desired to be carried out using these, it is necessary to preserve a large amount of primordial germ cells and to utilize them in developmental biotechnology.

On the other hand, when the conservation of species is carried out universally, it is necessary to develop the technique for cryopreservation of primordial germ cells and germ cells.

In particular, for the rare species which are in danger of extinction, such as Nipponia nippon, it is considered to be an urgent necessity to develop the technique of conserving the genetic material from the viewpoint of protecting the genetic resources.

In order to preserve germ-line cells, heretofore, sperms, eggs, fertilized eggs and early stage embryos have been freeze-stored in viviparous animals, such as mammals, etc., of which the eggs do not contain a large amount of yolk. However, this method is not always possible and the cryopreservation of fertilized eggs of some species is often difficult.

On the other hand, in oviparous animals such as birds, since the yolk in their eggs is a barrier to the freezing of their eggs, it has been said that the cryopreservation of germ-line cells except for spermatozoa is impossible.

SUMMARY OF THE INVENTION

The object of the present invention is to develop a method for cryopreservation of primordial germ cells or germ cells of birds so as to use them as materials for developmental biotechnology or for conservation of species, etc.

The present inventor has noted that primordial germ cells or germ cells before meiosis have various genetic informations and, as being different from eggs and sperms, have morphological forms and properties similar to somatic cells, though their morphological forms and properties differ from those of general somatic cells in many points.

Utilizing such a little difference between these, it is possible to separate and purify primordial germ cells obtained from embryos which are at particular development stages. The present inventor has confirmed that it is possible to suspend the thus-separated primordial germ cells or germ cells in a freezing medium, which are then stored at ultra-low temperatures using liquid nitrogen or the like and thereafter thawed by suitable means and that, after having confirmed the existence of the cells, it is possible to use the cells as materials for developmental biotechnology or for conservation of species, etc. On the basis of these confirmations, the present inventor has attained the present invention.

Specifically, the present invention relates to a method for cryopreservation of primordial germ cells and germ cells, which is characterized in that primordial germ cells or germ cells before meiosis that have been separated from embryos of birds are suspended in a freezing medium containing a cryoprotective agent and then frozen and stored therein.

DETAILED DESCRIPTION OF THE INVENTION

In the present invention, used are primordial germ cells or germ cells before meiosis that have been separated from embryos, especially early stage embryos, of birds. As birds, preferred are fowls such as chickens, quails, turkeys, ducks, etc. It is also possible to apply the method of the present invention to the cells separated from the embryos of other oviparous animals and viviparous animals, such as insects, fishes, amphibians, reptiles, mammals, etc., than birds.

The primordial germ cells and the germ cells to which the cryopreservation method of the present invention is applied are primordial germ cells and germ cells before meiosis that are derived from the extraembryonic tissue and the blood of embryos or from the further developed gonadal primordia thereof.

These cells can be dissociated by ordinary methods. For example, general methods for dissociating them are described in Freshney, R. I., Culture of Animal Cells, 2nd Edition, Alan R. Liss Inc., New York (1987).

Primordial germ cells exist in various sites, depending on their development stages. At the initial stage, they exist in the extraembryonic site, which is referred to as a germinal crescent; then, with further development, they begin to circulate in the blood; and soon, with the generation of so-called germinal ridge, they migrate in the site to be gonadal primordia.

Therefore, since primordial germ cells exist in various sites, depending on the development stages, the method for separating such primordial germ cells must be selected suitably in accordance with the varying development stages.

For instance, when these cells are separated from the embryonic tissue, the cells must be dissociated from the collected tissue by treatment with trypsin or by pipetting or must be separated from somatic cells by centrifugation. On the other hand, when these cells are separated from the blood, the blood is collected from the early stage embryos, using a glass needle or the like, this is suspended in a culture medium, and then the primordial germ cells are separated from the hemocytes by density gradient centrifugation using Ficoll (Yasuda, Y. et al., Journal of Reproduction and Fertility, 96, 521–528 (1992)) to obtain a concentrated fraction of the cells.

As the culture medium in which the cells to be separated are suspended, any conventional one can be employed. For instance, employable are a culture medium containing 10% fetal calf serum (DMEM, Hanks, M199, cHanks': Yasuda Y. et al., Journal of Reproduction and Fertility, 96, 521–528

(1992), etc.), a phosphate buffered saline (PBS), a phosphate buffered saline containing neither calcium nor magnesium (PBS(−)), etc.

As the freeze-storing (preserving) medium, used is a culture medium containing 10% of fetal calf serum that has been adjusted to contain a cryoprotective agent, such as dimethylsulfoxide (DMSO), glycerol, 1,2-propanediol, ethylene glycol, propylene glycol, acetamide, sucrose, raffinose, etc., generally at a final concentration of from 10 to 90%, preferably from 10 to 20% (DMEM, Hanks, M199, cHanks'; Yasuda Y. et al., Journal of Reproduction and Fertility, 96, 521–528 (1992), etc.). DMSO is preferred for the method of the present invention.

To freeze the cells, employable is either an ordinary slow freezing method or an ordinary rapid freezing method. For instance, employable is a freezing method in which the cells are cooled to −80° C. at a cooling speed of 1° C./min, then put into a liquid nitrogen at −196° C. and frozen and stored in the liquid nitrogen.

Next, one embodiment of the present invention will be described below, using chickens.

The process of the development of the embryos of chickens generally comprises stages I to X in the bodies of parents before oviposition [Eyal-Giladi, H. and Kochav, S., Developmental Biology, 49, 321–337 (1976)] and stages 1 to 45 during incubation after oviposition [Hamburger, V. and Hamilton, H. L., Journal of Morphology, 88, 49–92 (1951)]. In the present invention, preferably used are the embryos at stages 1 to 36, especially preferably at stages 4 to 30, more preferably at stages 4 to 10, 12 to 18 and 26 to 30.

To separate the primordial germ cells from the early stage embryos of chickens, the following processes can be employed.

(1) To separate the primordial germ cells from the germinal crescent:

The tissue constituting the germinal crescent in the embryos at stages 4 to 10 is cut and separated, and then the cells therein are dissociated by treatment with trypsin or by pipetting or the like and suspended in a culture medium containing 10% of fetal calf serum (DMEM, Hanks, cHanks', M199, etc.) to obtain a cell fraction containing the primordial germ cells.

(2) To separate the primordial germ cells from the blood:

The blood is collected from the embryos at stages 12 to 18, using a glass needle or the like, and then suspended in a culture medium containing 10% fetal calf serum (DMEM, Hanks, cHanks', M199, etc.).

Afterwards, the resulting suspension is subjected to density gradient centrifugation using Ficoll [Yasuda Y. et al., Journal of Reproduction and Fertility, 96, 521–528 (1992)], by which the primordial germ cells are separated from hemocytes, to obtain a concentrated fraction of the cells.

This fraction contains about 40% of hemocytes, which, however, cause no problem in practical use.

Next, this fraction is suspended in a culture medium containing 10% of fetal calf serum that has been adjusted to contain a cryoprotective agent, such as dimethylsulfoxide, etc., generally at a final concentration of from 10 to 90%, preferably from 10 to 20% (DMEM, Hanks, cHanks', M199, etc.), and the resulting suspension is put into a freezing tube and cooled to −80° C. at a cooling speed of 1° C./min, which is then put into a liquid nitrogen at −196° C. and frozen and stored therein.

To separate the primordial germ cells or germ cells before meiosis from the gonadal primordia or the gonads of the embryos, the following process may be employed.

The embryos at stages 23 to 36, preferably at stages 26 to 30 are put into a phosphate buffered saline (PBS) or the like, preferably a phosphate buffered saline containing neither calcium nor magnesium (PBS(−)), in which the adhered yolk and others are washed off therefrom.

Afterwards, using a dissection microscope, the gonads or the gonadal primordia that exist along with the left and right kidneys while adhering thereto are separated and put into PBS(−).

In this way, the gonads or the gonadal primordia are collected from the embryos and are cut into fine pieces. After thus cut, these fine pieces are subjected to centrifugation, for example, under the condition of 800 ×g for 5 minutes, the resulting supernatant is removed, and PBS(−) containing 0.25% of trypsin is added to the residue. This is then incubated at 37° C. for 5 minutes, from which the cells of the gonads or the gonadal primordia are dissociated by pipetting. The thus-prepared cell suspension contains the primordial germ cells or the germ cells along with somatic cells derived from the gonads or the gonadal primordia.

This is further centrifuged under the condition of 800 ×g for 10 minutes, the resulting supernatant is removed, and the residual fraction is suspended in a culture medium containing 10% of fetal calf serum that has been adjusted to contain a cryoprotective agent, such as DMSO, etc., generally at a final concentration of from 10 to 90%, preferably from 10 to 20% (DMEM, Hanks, cHanks', M199, etc.). The thus-prepared suspension is put into a freezing tube and cooled to −80° C. at a cooling speed of 1° C./min, which is then put into a liquid nitrogen at −196° C. and frozen and stored therein, in the same manner as above.

According to the method of the present invention, the frozen primordial germ cells and germ cells can be stored for a desired period of time, for example, for 4 to 5 months or more. The cells thus frozen and stored in the freezing tube can be thawed in water at 4° C. The thus-thawed cells are morphologically normal. These were tested by Trypan Blue exclusion method with the result that the percentage of the living cells was from 85.7 to 98.0%.

When the cells freeze-stored by the method of the present invention are be used, the freezing tube that has been stored in the liquid nitrogen while containing the frozen cells therein is taken out from the liquid nitrogen and immediately put into water at about 4° C. whereby the cells are thawed therein. The thus-thawed cell suspension is tested by Trypan Blue exclusion method, by which the existence of the living cells can be confirmed.

Next, the present invention will be described in more detail by means of the following examples, which, however, are not intended to restrict the scope of the present invention.

EXAMPLE 1

From cryopreserved primordial germ cells, individuals were produced according to the process mentioned below.

(1) Collection and cryopreservation of Primordial Germ Cells:

Fertilized eggs of White Leghorns and those of Barred Plymouth Rocks were incubated at 38° C. for about 53 hours.

After breaking the thus-incubated eggs, about 50 μl of the blood were collected from 70 embryos at stages 13 to 15 and were suspended in 200 μl of a culture medium containing 10% of fetal calf serum [cHanks': Yasuda Y. et al., Journal of Reproduction and Fertility, 96, 521–528 (1992)].

The resulting suspension was subjected to density gradient centrifugation using Ficoll (mentioned above), by which the primordial germ cells were separated from hemocytes, to obtain about 40 μl of a concentrated fraction of the primordial germ cells.

Next, 40 μl of a culture medium that had been adjusted to contain DMSO at a final concentration of 10% (cHanks') were added to this fraction, mixed and put into a freezing tube, which was then cooled to −80° C. at a cooling speed of 1° C./min, then put into a liquid nitrogen at −196° C. and frozen and stored therein for 4 to 5 months.

(2) Preparation of Recipient Embryos:

In order to make easy the transplantation of the primordial germ cells, the recipient embryos were transferred into the culture system using surrogate eggshells.

Each of the fertilized eggs of White Leghorns and those of Barred Plymouth Rocks was broken, and only the yolk was transferred to a small eggshell, which was then filled with a thin albumen. Then, the opening of the eggshell was sealed with a wrapping film and plastic rings.

In this condition, the eggs were incubated at 38° C. for 53 hours, and after the embryos reached stages 14 to 15, from 4 to 10 μl of the blood were drawn out from each embryo, using a glass needle. The number of the primordial germ cells in the blood was counted.

Afterwards, the eggshells were again sealed and the eggs were incubated at 38° C. for 4 to 5 hours. These were used as recipient embryos.

(3) Transplantation of Primordial Germ Cells:

The freezing tube that had been stored in the liquid nitrogen was taken out therefrom and immediately put into water at 4° C., whereby the primordial germ cells stored in the tube were thawed.

The thus-thawed primordial germ cells were morphologically normal, and the percentage of the living cells was measured by Trypan Blue exclusion method to be 94.2%.

The primordial germ cells can easily be distinguished from hemocytes with a microscope, as the two are morphologically different from each other. Using an inverted microscope and a glass needle, 100 thawed primordial germ cells were picked up and then suspended in about 1 μl of a culture medium containing 10% of fetal calf serum (cHanks'), and the resulting suspension was injected into the bloodstream of the recipient embryos. The thus-transplanted primordial germ cells were able to migrate in the genital ridges of the recipient embryos.

Each of the thus-transplanted recipient embryos was transferred to a large eggshell and incubated at 38° C. for about 18 days to hatching. The hatchability was 22.0%. These chickens were reared by an ordinary method to obtain matured chickens (germ-line chimeras).

(4) Production of Frozen-and-Thawed Primordial Germ Cells-Derived Offspring from Germ-Line Chimeras (progeny test):

The recipient embryos into which the frozen and thawed primordial germ cells had been transferred were incubated to hatch chickens, which were matured. These matured individuals (germ-line chimeras) were subjected to a cross test.

Regarding the color of feathers, White Leghorns have a dominant gene (I/I) of preventing a black pigmentation from depositing on their feathers, while Barred Plymouth Rocks do not have this gene (i/i). Therefore, from the color of the feathers of the chickens to be obtained by crossing the produced germ-line chimera and a Barred Plymouth Rock, it is possible to distinguish the individuals derived from the transferred primordial germ cells.

For this reason, the progeny test was carried out by crossing the germ-line chimera and a Barred Plymouth Rock, in which the black chickens were referred to as the transferred primordial germ cells-derived chickens in the case when the donor cells were of a Barred Plymouth Rock, while the white chickens (often having black spots) were referred to as the same in the case when the donor cells were of a White Leghorn.

The results are shown in Table 1 and Table 2. Table 1 indicates the results of the progeny test of the germ-line chimeras produced by transferring the freeze-stored and thawed primordial germ cells of a Barred Plymouth Rock into the early stage embryos of a White Leghorn; while Table 2 indicates the results of the progeny test of the germ-line chimeras produced by transferring the freeze-stored and thawed primordial germ cells of a White Leghorn into the early stage embryos of a Barred Plymouth Rock.

From the germ-line chimeras, the transferred primordial germ cells-derived individuals were obtained at a proportion of from 1 to 26%, from which it is known that the freeze-stored and thawed primordial germ cells maintained the capacity of developing the individuals.

In these tables, the "test period" means the period of the cross test. In the cross test, when male chickens were hatched from the transferred and incubated eggs, these were crossed with three female chickens to produce offspring, from which the proportion of producing the chickens derived from the transferred primordial germ cells was obtained. On the other hand, when female chickens were hatched from the transferred and incubated eggs, these were subjected to artificial insemination to produce offspring, from which the proportion of producing the chickens derived from the transferred primordial germ cells was tested.

TABLE 1

| Chicken No. | Test Period (week) | Number of Hatched Chickens | Number of Chickens derived from transferred Primordial Germ Cells | Proportion of Chickens derived from transferred Primordial Germ Cells (%) |
|---|---|---|---|---|
| Male | | | | |
| W-8259 | 34 | 462 | 28 | 6.1 |
| W-8260 | 28 | 338 | 41 | 12.1 |
| W-8261 | 34 | 464 | 4 | 0.9 |
| W-8262 | 14 | 123 | 32 | 26.0 |
| W-8265 | 34 | 472 | 23 | 4.9 |

TABLE 2

| Chicken No. | Test Period (week) | Number of Hatched Chickens | Number of Chickens derived from transferred Primordial Germ Cells | Proportion of Chickens derived from transferred Primordial Germ Cells (%) |
|---|---|---|---|---|
| Male | | | | |
| W-8267 | 10 | 121 | 21 | 17.4 |
| Female | | | | |
| W-8268 | 4 | 4 | 1 | 25.0 |
| W-8269 | 4 | 7 | 1 | 14.3 |
| W-8272 | 4 | 14 | 1 | 7.1 |

One male chickens and two female chickens derived from frozen-thawed primordial germ cells were further grown and matured and then these were crossed to investigate their reproductive performance.

The crossing was conducted every week by artificial insemination, and the eggs produced were collected for 10 weeks, from which the fertility and the hatchability were tested.

As a result, the fertility by the crossing was 86.5% and the hatchability of the fertilized eggs was 81.7%, from which it is known that the chickens derived from frozen-thawed primodial germ cells had normal reproductive performance.

EXAMPLE 2

(1) Collection and Freeze-Storing of Germ Cells before Meiosis:

Fertilized eggs of White Leghorns and those of Barred Plymouth Rocks were incubated at 38° C. for about 4.5 days to obtain embryos at stages 23 to 25.

After breaking the thus-incubated eggs, the embryos were put into a phosphate buffered saline containing neither calcium nor magnesium (PBS(−)), in which the adhered yolk and others were washed of therefrom.

Afterwards, using a dissection microscope, the gonadal primordia that existed along with the left and right kidneys while adhering thereto were separated and put into PBS(−).

In this way, from 15 to 20 gonadal primorida were collected from the embryos and were cut into fine pieces. After thus cut, these fine pieces were subjected to centrifugation under the condition of 800×g for 5 minutes, the resulting supernatant was removed, and 200 μl of PBS(−) containing 0.25% of trypsin was added to the residue. This was then incubated at 37° C. for 5 minutes, from which the cells of the gonadal primordia were dissociated by pipetting. The thus-prepared cell suspension contained germ cells along with somatic cells derived from the gonadal primordia.

One ml of a culture medium containing 10% of fetal calf serum (DMEM) was added to the suspension, mixed and then centrifuged at 800×g for 10 minutes, and the resulting supernatant was removed.

Next, 40 μl of a culture medium containing 10% of fetal calf serum (DMEM) that had been prepared to contain DMSO at a final concentration of 10% were added to the residue and mixed, and the resulting mixture was put into a freezing tub and cooled to −80° C. at a cooling speed of 1° C./min, which was then put into a liquid nitrogen at −196° C. and frozen and stored therein for 1 to 2.

(2) Thawing of Germ Cells before Meiosis:

The freezing tube that had been stored in the liquid nitrogen was taken out therefrom and immediately put into water at 4° C., whereby the germ cells before meiosis stored in the tube were thawed.

After thus thawed, the living cells in the thawed cells was measured by Trypan Blue exclusion method to be 92.0%.

The method of the present invention is applied to primordial germ cells and germ cells before meiosis having various genetic informations. It is therefore expected that the method of the present invention is employable for conservation of species of birds, for protection of rare species which are in danger of extinction, such as Nipponia nippon, and also for production of transgenic animals, production of novel gene marker animals on cell levels, production of disease model animals, production of useful substances by gene engineering and development of test methods for toxicity to germline cells.

While the invention has been described in detail and with reference to specific embodiments thereof, it will be apparent to one skilled in the art that various changes and modifications can be made therein without departing from the spirit and scope thereof.

What is claimed is:

1. A method for cryopreservation of primordial germ cells and germ cells, wherein primordial germ cells or germ cells before meiosis that have been separated from an embryo of a bird during incubation are suspended in a freeze-storing medium containing a cryoprotective agent and then the cells in said medium are frozen and stored, wherein said embryo of the bird is at stage 4 to 30, according to the classification scheme of Hamburger and Hamilton.

2. The method as claimed in claim 1, wherein said bird is a fowl.

3. The method as claimed in claim 2, wherein said fowl is selected from the group consisting of chickens, quails, turkeys, and ducks.

4. The method as claimed in claim 1, wherein said primordial germ cells or germ cells before meiosis are obtained from an embryonic germinal crescent, blood or gonadal primordium separated from a yolk-free embryo.

5. The method as claimed in claim 1, wherein said primordial germ cells are cells separated from a germinal crescent of a chicken embryo at stage 4 to 10.

6. The method as claimed in claim 1, wherein said primordial germ cells are cells separated from blood of an initial embryo of a chicken at stage 12 to 18.

7. The method as claimed in claim 1, wherein said primordial germ cells or said germ cells before meiosis are cells separated from gonadal primordium or gonads of a chicken embryo at stage 23 to 30.

* * * * *

UNITED STATES PATENT AND TRADEMARK OFFICE
CERTIFICATE OF CORRECTION

PATENT NO.  : 5,759,763
DATED       : June 2, 1998
INVENTOR(S) : Mitsuru NAITO, et al.

It is certified that error appears in the above-identified patent and that said Letters Patent is hereby corrected as shown below:

On the title page, Item [30], the Foreign Application Priority Data is incorrect. It should read:

--Oct. 31, 1994   [JP]   Japan..........6-288638--

Signed and Sealed this

Second Day of February, 1999

Attest:

Attesting Officer

*Acting Commissioner of Patents and Trademarks*